United States Patent
Kim et al.

(10) Patent No.: US 8,343,736 B2
(45) Date of Patent: Jan. 1, 2013

(54) XYLITOL PRODUCING MICROORGANISM INTRODUCED WITH ARABINOSE METABOLIC PATHWAY AND PRODUCTION METHOD OF XYLITOL USING THE SAME

(75) Inventors: Jung Hoe Kim, Daejeon (KR); Byoung Hoon Yoon, Daejeon (KR); Woo Young Jeon, Daejeon (KR); Woo Yong Shim, Daejeon (KR)

(73) Assignee: Korea Advanced Institute of Science and Technology (KR)

( * ) Notice: Subject to any disclaimer, the term of this patent is extended or adjusted under 35 U.S.C. 154(b) by 0 days.

(21) Appl. No.: 13/391,073

(22) PCT Filed: Jan. 18, 2011

(86) PCT No.: PCT/KR2011/000346
§ 371 (c)(1),
(2), (4) Date: Feb. 17, 2012

(87) PCT Pub. No.: WO2012/046924
PCT Pub. Date: Apr. 12, 2012

(65) Prior Publication Data
US 2012/0171739 A1    Jul. 5, 2012

(30) Foreign Application Priority Data
Oct. 6, 2010  (KR) .................. 10-2010-0097335

(51) Int. Cl.
C12P 21/06    (2006.01)
C12N 15/19   (2006.01)
C12N 1/00    (2006.01)
C12N 15/00   (2006.01)

(52) U.S. Cl. ............... 435/69.1; 435/69.2; 435/320.1; 435/254.22

(58) Field of Classification Search ............. 435/69.1, 435/69.2, 320.1, 254.22
See application file for complete search history.

(56) References Cited

U.S. PATENT DOCUMENTS

| 7,745,177 B2 | 6/2010 | Kim et al. | |
| 7,820,414 B2 * | 10/2010 | Kim et al. | 435/105 |
| 7,977,083 B1 * | 7/2011 | Sakakibara et al. | 435/243 |
| 2009/0004704 A1 | 1/2009 | Kim et al. | |

FOREIGN PATENT DOCUMENTS

| KR | 95-37516 | 7/1998 |
| KR | 1019960013638 | 10/1998 |
| KR | 1996-030577 | 11/1998 |
| KR | 1019980020034 | 3/2000 |
| KR | 10-2005-0079751 | 3/2007 |
| KR | 10-2009-0013617 | 2/2009 |

OTHER PUBLICATIONS

Granström, T. B. et al. (2007), "A rare sugar xylitol. Part I: the biochemistry and biosynthesis of xylitol", Appl. Microbiol. Biotechnol. 74:277-281.
Hahn-Hägerdal, B. et al. (1994), "Biochemistry and physiology of xylose fermentation by yeast", Enzyme Microb. Technol., 16:933-943.
Kim, S. Y. et al. (1997), "Improvement of Xylitol Production by Controlling Oxygen Supply in *Candida parapsilosis*", J. Ferment. Bioeng., 83(3):267-270.
Laplace, J. M. et al. (1991), "Alcoholic fermentation of glucose and xylose by *Pichia stipitis, Candida shehatae, Saccharomyces cerevisiae* and *Zymomonas mobilis*: oxygen requirement as a key factor", Appl. Microbiol. Biotechnol., 36:158-162.
Winkelhausen, E. et al. (1998), "Microbial Conversion of D-Xylose to Xylitol", J. Ferment. Bioeng. 86:1-14.
Becker et al. (Jul. 2003), "A Modified *Saccharomyces cerevisiae* Strain That Consumes L-Arabinose and Produces Ethanol," Applied and Environmental Microbiology, vol. 69. No. 7, pp. 4144-4150.
Kawaguchi et al. (2008), "Engineering of an L-arabinose metabolic pathway in *Corynebacterium glutamicum*," Applied Microbiology and Biotechnology, 77:1053-1062.
Ko et al. (Jun. 2006), "Production of Xylitol from D-Xylose by a Xylitol Dehydrogenase Gene-Disrupted Mutant of *Candida tropicalis*," Applied and Environmental Microbiology, vol. 72, No. 6, pp. 4207-4213.
Weidemann et al. (Apr. 2008), "Codon-Optimized Bacterial Genes Improve L-Arabinose Fermentation in Recombinant *Saccharomyces cerevisiae*," Applied and Environmental Microbiology, vol. 74, No. 7, pp. 2043-2050.

* cited by examiner

*Primary Examiner* — Karen Cochrane Carlson
(74) *Attorney, Agent, or Firm* — Greenlee Sullivan P.C.

(57) ABSTRACT

The present invention relates to an efficient production method of xylitol by using the xylitol producing microorganism introduced with arabinose metabolic pathway to inhibit the production of arabitol, the byproduct, and instead to use arabinose only for cell metabolism in xylose/arabinose mixed medium. More precisely, to express efficiently L-arabinose isomerase (araA), L-ribulokinase (araB) and L-ribulose-5-phosphate 4-epimerase (araD) in *Candida tropicalis*, codon optimization was performed. Then, each gene was inserted in the gene expression cassette containing the glyceraldehyde-3-phosphate dehydrogenase promoter and the selection marker URA3, which was introduced into *Candida* sp. microorganism. As a result, arabitol, the byproduct interrupting the purification and crystallization of xylitol could be inhibited, making the production method of xylitol of the present invention more efficient. The xylitol producing microorganism introduced with arabinose metabolic pathway of the present invention can be effectively used for the production of xylitol with high productivity by inhibiting the generation of arabitol.

13 Claims, 2 Drawing Sheets

PGtrpfs2-CoAraA

PAHfs-CoAraB

PAHfs2-CoAraD

XYLITOL PRODUCING MICROORGANISM INTRODUCED WITH ARABINOSE METABOLIC PATHWAY AND PRODUCTION METHOD OF XYLITOL USING THE SAME

CROSS-REFERENCE TO RELATED APPLICATIONS

This application is a U.S. National Stage Application under 35 U.S.C. §371 of International Application No. PCT/KR2011/000346, filed Jan. 18, 2011, which claims the benefit of Korean Application No.10-2010-0097335, filed Oct. 6, 2010. Both of these applications are hereby incorporated by reference in their entireties.

BACKGROUND OF THE INVENTION

1. Field of the Invention

The present invention relates to a xylitol producing microorganism introduced with arabinose metabolic pathway and a method for producing xylitol efficiently by using the same, more precisely a xylitol producing microorganism introduced with arabinose metabolic pathway to inhibit the generation of arabitol that interrupts the purification and crystallization of xylitol and at the same time to utilize arabinose for cell growth, and a production method of xylitol with high productivity by using the same.

2. Description of the Related Art

Xylitol is the pentose sugar alcohol having high sweetness, which thus has been widely used as a functional sweetener that can take the place of sugar. Xylitol has the sweetness similar to sugar, but its metabolic process in human body is not related with insulin. Therefore, xylitol has been used as an alternative sweetener of sugar for diabetics. In particular, xylitol has the activity of inhibiting the growth of *Streptococcus mutans*, the cariogenic bacteria, so that it is also widely used as an anticariogenic material.

Xylitol is produced by chemical-reducing hemicellulose hydrolysates containing lots of xylose, such as corncob and sugar cane stalk. However, such chemical method does not favor the separation and purification of xylose from other pentose and hexose such as arabinose and glucose, etc, and has disadvantages of high cost for the separation and purification and as low xylose recovery rate as 50~60%. In addition, such chemical method is also characterized by high temperature/high pressure procedure using hydrogen gas and nickel catalyst, delivering issues of high risk and environmental problem.

To overcome the above disadvantages or problems of the conventional chemical method, a biological approach has been actively made to produce xylitol. Unlike the chemical method, the biological method can utilize xylose even with low purity as a raw material and the procedure itself can be completed at room temperature under normal pressure, suggesting that the biological method is pro-environmental production process. To produce xylitol with high productivity and high yield using the biological method, various bacteria, yeast, fungi, recombinant yeast, etc, have been studied (Winkelhausen, E. et al., *J. Ferment. Bioeng.* 86:1-14, 1998; Granstrom, T. B. et al., *Appl. Microbiol. Biotechnol.* 74:277-281, 2007). However, bacteria and recombinant yeast have been confirmed not to be appropriate for the industrial production of xylitol because their xylose metabolic pathways are too weak or not very efficient. On the other hand, among many yeast/fungi, *Candida* sp. strains show high capacity to utilize xylose, compared with other microorganisms, making them promising candidates for the biological production of xylitol with high productivity and high yield.

According to the previous studies, *Candida* sp. strains such as *C. guillermondi, C. parapsilosis*, and *C. tropicalis* can convert xylose introduced from outside of the cell into xylitol with the help of xylose reductase, and further can convert the produced xylitol into xylulose with the help of xylitol dehydrogenase. The xylulose can be further converted into xylulose-5-phosphate by xylulokinase and be consumed for the cell growth and maintenance via pentose phosphate pathway (Laplace, J. M. et al., *Appl. Microbiol. Biotechnol.*, 36:158-162, 1991; Hahn-Hagerdal, B. et al., *Enzyme Microb. Technol.*, 16:933-943, 1994).

At this time, the xylose reductase uses NADPH (nicotinamide adenine dinucleotide phosphate) as a cofactor, and the xylitol dehydrogenase uses $NAD^+$ (nicotinamide adenine dinucleotide) as a cofactor. Xylitol converted from xylose mediated by xylose reductase is converted again into xylulose by xylitol dehydrogenase. At this time, if oxygen supply is limited in a medium to make the concentration of dissolved oxygen to be 0.5%~2.0%, intracellular redox imbalance is induced, which means $NAD^+$, the cofactor needed by xylitol dehydrogenase, becomes short, resulting in the inhibition of the conversion of xylitol into xylulose. As a result, xylitol is accumulated in cells and medium, indicating that xylitol is produced from xylose with the yield of 50~60%. That is, in the conventional method to produce xylitol by using a xylitol producing microorganism, it is necessary to regulate dissolved oxygen to the degree of low concentration by limiting oxygen supply (limited aeration). So, studies have been actively undergoing to increase xylitol productivity with high yield by inducing intentional imbalance of oxidation reduction potential in cells by maintaining dissolved oxygen concentration low by limited aeration (Kim, S. Y. et al., *J. Ferment. Bioeng.*, 83(3):267-270, 1997; Korean Patent No. 1996-030577).

Korean Patent No. 10-0169061 describes a method for producing xylitol by using concentrated *Candida parapsilosis* strain with regulating the concentration of dissolved oxygen to 0.8~1.2%. However, it is actually almost impossible to regulate the concentration of dissolved oxygen as low as the above when xylitol is produced in a large industrial scale by using a large volume fermenter and if possible, the yield cannot exceed 50~60%. Korean Patent No. 10-0259470 describes a stirring speed to regulate oxygen level in a medium under 1% DOT (oxygen concentration in a medium presented as %). However, there is still inconvenience in the process. Korean Patent Application No. 95-37516 describes a production method of xylitol by using a transformant strain of *Candida parapsilosis*, in which xylitol production optimization achieved by the regulation of oxygen partial pressure in the medium is described. Korean Patent Application No. 96-13638 describes the optimum medium and culture conditions for the production of xylitol from the said transformant strain. However, in this method, the yield of xylitol was not more than 70% even under the optimum conditions. The present inventors have developed a *Candida tropicalis* transformant in which xylitol dehydrogenase activity is completely inactivated, based on the fact that xylitol produced in *Candida* sp. strain is converted into xylulose by xylitol dehydrogenase (Korean Patent No. 10-0730315). According to the previous methods, limited aeration in the medium was necessary to induce intracellular oxidation reduction potential imbalance, in order to inhibit the activity of xylitol dehydrogenase converting xylitol into xylulose. However, in the transformant in which xylitol dehydrogenase is inactivated, xylitol produced from xylulose is not used for cell growth anymore, suggesting that oxidation reduction potential imbalance is not needed. By this method, xylose can be converted into xylitol with the yield of 97-98%.

Even though the yield of xylitol from xylose was maximized, there is another problem to solve, which is that biomass hydrolysate, used as the raw material for the production of xylitol, contains not only xylose but also a huge amount of arabinose. Xylose reductase in the xylitol producing microorganism affects arabinose as well. So, when the biomass hydrolysate is directly used as a law material, arabitol is also produced. Arabitol, the pentose sugar alcohol like xylitol, has similar molecular structure and physical properties to xylitol. It is thus unwanted byproduct that lowers production rate of xylitol by interrupting purification and crystallization of xylitol. Therefore, when xylose/arabinose mixed medium is used for the production of xylitol, a novel technique to produce xylitol without producing arabitol is required.

The present inventors performed codon optimization to express efficiently the arabinose metabolic pathway involved enzymes such as L-arabinose isomerase (araA), L-ribulokinase (araB), and L-ribulose-5-phosphate 4-epimerase (araD) in *Candida* sp. Then, each gene was inserted in the cassette containing glyceraldehyde-3-phosphate dehydrogenase promoter and URA3, the selection marker. The prepared cassette was introduced in *Candida* sp. As a result, the present inventors completed this invention by confirming that xylitol can be produced with high productivity by inhibiting the production of arabitol interrupting the purification and crystallization of xylitol.

SUMMARY OF THE INVENTION

It is an object of the present invention to provide a xylitol producing microorganism facilitating maximization of xylitol production yield by inducing arabinose metabolic pathway to inhibit arabitol generation and to use arabinose for the cell growth.

It is another object of the present invention to provide a production method of the said xylitol producing microorganism.

It is also an object of the present invention to provide a production method of xylitol with high productivity in the medium using glucose or glycerol as a carbon source by using the said xylitol producing microorganism.

To achieve the above objects, the present invention provides a xylitol producing microorganism in which arabitol generation is inhibited, prepared by introducing a gene expression cassette containing an arabinose metabolic pathway related gene into a *Candida* sp. strain.

The present invention also provides a production method of the xylitol producing microorganism in which arabitol generation is inhibited, prepared by introducing a gene expression cassette containing an arabinose metabolic pathway related gene into a *Candida* sp. strain.

The present invention further provides a mass-production method of xylitol, comprising the following steps:
1) culturing the xylitol producing microorganism in the medium containing biomass hydrolysate and a carbon source;
2) producing xylitol from the cultured microorganism; and
3) separating xylitol from the culture solution.

Advantageous Effect

As explained hereinbefore, the present invention relates to an efficient production method of xylitol characterized by using a xylitol producing microorganism introduced with arabinose metabolic pathway to inhibit arabitol, the byproduct, and to use arabinose for cell metabolism in the xylose/arabinose mixed medium. This method of the present invention can be effectively used for the production of xylitol with high productivity by inhibiting the generation of arabitol interrupting the purification and crystallization of xylitol.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Hereinafter, the present invention is described in detail.

The present invention provides a xylitol producing microorganism in which arabitol generation is inhibited, prepared by introducing a gene expression cassette containing an arabinose metabolic pathway related gene into a *Candida* sp. strain.

The present invention also provides a xylitol producing microorganism in which arabitol generation is inhibited, prepared by introducing the gene expression cassettes of the below 1)~3) into a *Candida* sp. strain:
1) gene expression cassette composed of a promoter, a polynucleotide encoding L-arabinose isomerase, and a terminator;
2) gene expression cassette composed of a promoter, a polynucleotide encoding L-ribulokinase, and a terminator; and
3) gene expression cassette composed of a promoter, a polynucleotide encoding L-ribulose-5-phosphate 4-epimerase, and a terminator.

The promoter hereinabove preferably has the nucleotide sequence represented by SEQ ID NO: 1, the polynucleotide encoding L-arabinose isomerase hereinabove preferably has the nucleotide sequence represented by SEQ ID NO: 7, the polynucleotide encoding L-ribulokinase hereinabove preferably has the nucleotide sequence represented by SEQ ID NO: 8, the polynucleotide encoding L-ribulose-5-phosphate 4-epimerase hereinabove preferably has the nucleotide sequence represented by SEQ ID NO: 9, and the terminator hereinabove preferably has the nucleotide sequence represented by SEQ ID NO: 2, but not always limited thereto.

The present invention also provides a xylitol producing microorganism in which arabitol generation is inhibited, which is deposited at Korean Collection for Type Cultures (KCTC), Korea Research Institute of Bioscience and Biotechnology (KRIBB) on Sep. 8, 2010 (Accession No: KCTC 11761BP).

The said xylitol producing microorganism PBDAU, LBDAU or EBDAU in which arabitol generation is inhibited, can be prepared by the following steps: constructing the gene expression cassette composed of a promoter having the nucleotide sequence represented by SEQ ID NO: 1, a polynucleotide having the nucleotide sequence represented by SEQ ID NO: 7, and a terminator having the nucleotide sequence represented by SEQ ID NO: 2; constructing the gene expression cassette composed of a promoter having the nucleotide sequence represented by SEQ ID NO: 1, a polynucleotide having the nucleotide sequence represented by SEQ ID NO: 8, and a terminator having the nucleotide sequence represented by SEQ ID NO: 2; constructing the gene expression cassette composed of a promoter having the nucleotide sequence represented by SEQ ID, NO: 1, a polynucleotide having the nucleotide sequence represented by SEQ ID NO: 9, and a terminator having the nucleotide sequence represented by SEQ ID NO: 2; and introducing the said gene expression cassette into a Candida sp. strain, but not always limited thereto.

The Candida sp. strain herein is preferably selected from the group consisting of Candida guillermondi (C. guillermondi), Candida parapsilosis (C. parapsilosis) and Candida tropicalis (C. tropicalis), but not always limited thereto.

The Candida tropicalis is preferably the one in which xylitol dehydrogenase is inactivated, but not always limited thereto.

The Candida tropicalis in which xylitol dehydrogenase is inactivated is the microorganism deposited under the Accession No. KCTC 11137BP, but not always limited thereto.

The Candida tropicalis in which xylitol dehydrogenase is completely inactivated has the activity to arabinose contained in the biomass hydrolysate used as a raw material for xylitol production. The said Candida tropicalis does not have the metabolic pathway that uses arabinose as a carbon source. Therefore, once getting in cells, arabinose is converted into arabitol by non-specific activity of xylose reductase, but cannot be further metabolized and expelled out of the cell. So, if the biomass hydrolysate is directly used as a matrix, arabitol will be generated. Arabitol is pentose sugar alcohol like xylitol, and has similar molecular structure and physical properties to xylitol. So, it is an unwanted byproduct that lowers production yield of xylitol by interrupting purification and crystallization of xylitol. Therefore, it is required to develop a new production method of xylitol without generating arabitol by using xylose/arabinose mixed medium.

The present inventors introduced arabinose metabolic pathway of bacteria [L-arabinose isomerase (araA), L-ribulokinase (araB), and L-ribulose-5-phosphate 4-epimerase (araD)] into Candida tropicalis BSXDH-3, by which arabinose could be converted into xylulose-5-phosphate that could be used for cell metabolism via pentose phosphate pathway and glycolytic pathway.

To confirm whether or not arabinose metabolic pathway of the xylitol producing microorganism (PBDAU, LBDAU, and EBDAU) could inhibit the generation of arabitol interrupting the purification and crystallization of xylitol, the established microorganism was cultured in the arabinose minimal medium, followed by investigation of arabinose consumption rate and arabitol generation rate and dry cell weight over the time (see Tables 1, 2 and 3).

As a result, it was confirmed that the wild type Candida tropicalis (control) could not be growing in the minimal medium containing arabinose alone as a carbon source, while LBDAU, the xylitol producing microorganism, could be growing as much as 1.6 g/L of dry cell weight with consuming 4.3 g/L of arabinose for 60 hours. It was also confirmed that In the meantime, BSXDH-3 in which xylitol dehydrogenase was inactivated was confirmed not to be growing in the minimal medium containing arabinose alone as a carbon source and arabinose therein was not consumed and arabitol was not produced. It was also confirmed that PBDAU, the xylitol producing microorganism, could be growing as much as 2.1 g/L of dry cell weight with consuming 5.4 g/L of arabinose for 60 hours, and arabinose therein was not converted into arabitol and instead used for cell metabolism. Another control wild type Candida parapsilosis was confirmed not to be growing in the minimal medium containing arabinose alone as a carbon source, while the xylitol producing microorganism EBDAU was confirmed to be growing as much as 1.4 g/L of dry cell weight with consuming 4.1 g/L of arabinose for 60 hours, and arabinose therein was not converted into arabitol and instead used for cell metabolism.

Therefore, it was confirmed that the xylitol producing microorganism introduced with arabinose metabolic pathway of the present invention could be effectively used for the production of xylitol with high productivity by inhibiting the generation of arabitol.

The present invention also provides a production method of the xylitol producing microorganism in which arabitol generation is inhibited, prepared by introducing a gene expression cassette containing an arabinose metabolic pathway related gene into a Candida sp. strain.

The present invention also provides a xylitol producing microorganism in which arabitol generation is inhibited, prepared by introducing the gene expression cassettes of the below 1)~3) into a Candida sp. strain:

1) gene expression cassette composed of a promoter, a polynucleotide encoding L-arabinose isomerase, and a terminator;

2) gene expression cassette composed of a promoter, a polynucleotide encoding L-ribulokinase, and a terminator; and 3) gene expression cassette composed of a promoter, a polynucleotide encoding L-ribulose-5-phosphate 4-epimerase, and a terminator.

The promoter hereinabove preferably has the nucleotide sequence represented by SEQ ID NO: 1, the polynucleotide encoding L-arabinose isomerase hereinabove preferably has the nucleotide sequence represented by SEQ ID NO: 7, the polynucleotide encoding L-ribulokinase hereinabove preferably has the nucleotide sequence represented by SEQ ID NO: 8, the polynucleotide encoding L-ribulose-5-phosphate 4-epimerase hereinabove preferably has the nucleotide sequence represented by SEQ ID NO: 9, and the terminator hereinabove preferably has the nucleotide sequence represented by SEQ ID NO: 2, but not always limited thereto.

The present invention also provides a production method of the xylitol producing microorganism in which arabitol generation is inhibited, which is deposited at Korean Collection for Type Cultures (KCTC), Korea Research Institute of Bioscience and Biotechnology (KRIBB) on Sep. 8, 2010 (Accession No: KCTC 11761BP).

The Candida sp. strain herein is preferably selected from the group consisting of Candida guillermondi (C. guillermondi), Candida parapsilosis (C. parapsilosis) and Candida tropicalis (C. tropicalis), but not always limited thereto.

The Candida tropicalis is preferably the one in which xylitol dehydrogenase is inactivated, but not always limited thereto.

The Candida tropicalis in which xylitol dehydrogenase is inactivated is the microorganism deposited under the Accession No. KCTC 11137BP, but not always limited thereto.

The present inventors performed codon optimization to express efficiently the arabinose metabolic pathway involved enzymes such as L-arabinose isomerase (araA), L-ribulokinase (araB), and L-ribulose-5-phosphate 4-epimerase (araD) in Candida sp. Then, each gene was inserted in the cassette containing glyceraldehyde-3-phosphate dehydrogenase promoter and URA3, the selection marker. The prepared cassette was introduced in Candida sp. As a result, the present inventors completed this invention by confirming that xylitol can be produced with high productivity by inhibiting the production of arabitol interrupting the purification and crystallization of xylitol.

In a preferred embodiment of the present invention, codons of *Bacillus licheniformis* L-arabinose isomerase (araA), *Escherichia coli* L-ribulokinase (araB) and L-ribulose-5-phosphate 4-epimerase (araD) were replaced with *Candida* sp. preferred codons based on data of Codon Usage Database (www.kazusa.or.jp/codon/index.html), in order to optimize the codons represented by SEQ ID NO: 7, NO: 8 and NO: 9, leading to the synthesis of CoAraA (SEQ ID NO: 7), CoAraB (SEQ ID NO: 8) and CoAraD (SEQ ID NO: 9) (GENEART, Germany). The optimized genes were cloned in the cassette containing the promoter of glyceraldehyde-3-phosphate dehydrogenase, the selection marker URA3 and the repetitive sequence (glu or arg gene) for the elimination of the selection marker, resulting in the construction of PGtrpfs2-CoAraA, PAHfs-CoAraB, and PAHfs2-CoAraD. These constructed cassettes were introduced in a *Candida* sp. strain. As a result, the transformants *Candida tropicalis* PBDAU, *Candida tropicalis* LBDAU and *Candida parapsilosis* EBDAU each expressing CoAraA, CoAraB and CoAraD were obtained.

The present invention further provides a production method of xylitol with high productivity in the medium using glucose or glycerol as a carbon source by using the transformant PBDAU, LBDAU or EBDAU.

Particularly, the production method of xylitol of the present invention is preferably performed by the following steps, but not always limited thereto:

1) culturing the transformant of the present invention in the medium containing biomass hydrolysate and a carbon source;
2) producing xylitol from the cultured microorganism; and
3) separating xylitol from the culture solution.

In the above method, the biomass hydrolysate of step 1) is preferably the one selected from the group consisting of corn-cob hydrolysate, sugar cane hydrolysate, coconut byproduct and birch hydrolysate, but not always limited thereto, and any biomass containing xylose can be used.

In the above method, the carbon source of step 1) is preferably glucose or glycerol, but not always limited thereto, and any carbon source that can be used for microorganism culture can be used.

To investigate the xylitol productivity of PBDAU, LBDAU, or EBDAU, the present inventors measured the concentrations of xylose, xylitol, arabinose, and arabitol over the time (see Tables 4, 5, 6, 7, 8, 9, and 10). As a result, the xylitol productivity of PBDAU was confirmed to be 0.63 g/L/h, and the xylitol productivity of BSXDH-3 (control) was confirmed to be 0.55 g/L/h. So, the xylitol productivity of PBDAU was 15% higher than that of the control BSXDH-3. BSXDH-3 produced 11.4 g/L of arabitol for 60 hours, while PBDAU did not produce arabitol, the byproduct, and instead produced xylitol only. Regarding the xylitol productivity of LBDAU, the wild type strain demonstrated the xylitol productivity of 0.51 g/L/h and LBDAU showed the productivity of 0.59 g/L/h. So, the xylitol productivity of LBDAU was confirmed to be 15% higher than that of the wild type strain. The wild type strain produced 10.3 g/L of arabitol for 60 hours, while LBDAU did not produce arabitol, the byproduct, and instead produced xylitol only. Regarding the xylitol productivity of EBDAU, the wild type strain demonstrated the xylitol productivity of 0.44 g/L/h and EBDAU showed the productivity of 0.49 g/L/h. Thus, the xylitol productivity of EBDAU was confirmed to be 12% higher than that of the wild type strain. The wild type strain produced 9.8 g/L of arabitol for 60 hours, while EBDAU did not produce arabitol, the byproduct, and instead produced xylitol only. In addition, when xylitol was produced at a large scale from the biomass hydrolysate of PBDAU in a fermenter, the xylitol productivity of BSXDH-3 was 2.16 g/L/h, and the xylitol productivity of PBDAU was 2.28 g/L/h. BSXDH-3 produced 6.4 g/L of arabitol for 72 hours, while PBDAU did not produce the arabitol, the byproduct, at all, and instead produced xylitol alone.

Therefore, it was confirmed that the xylitol producing microorganism introduced with arabinose metabolic pathway of the present invention can be effectively used for the production of xylitol with high productivity by inhibiting the generation of arabitol. It was also confirmed that the method of the present invention can be used to produce xylitol at high concentration with high productivity by inhibiting the generation of arabitol even when biomass hydrolysate is used for the mass production of xylitol.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

EXAMPLE 1

Cloning of glyceraldehyde-3-phosphate dehydrogenase Promoter and Terminator

For the cloning of glyceraldehyde-3-phosphate dehydrogenase (GAPDH) promoter and terminator of *Candida tropicalis*, PCR was performed by using *Candida tropicalis* genomic DNA and the following primer set. As a result 1455 bp promoter sequence (SEQ ID NO: 1) and 309 bp terminator sequence (SEQ ID NO: 1) were obtained.

Promoter PCR [94° C. 30 sec., 30 cycles (94° C. 30 sec., 55° C. 1 min., 72° C. 1 min. 30 sec.), 72° C. 7 min.]:

```
PGAP-F (BglII):
                                        (SEQ ID NO: 3)
5'-agatctaacgtggtatggttgtaagaaac-3';
and PGAP-R (XbaI_BamHI):
                                        (SEQ ID NO: 4)
5'-ggatccgcgtctagatgtttaaattctttaattg-3'.
```

Terminator PCR [94° C. 30 sec., 30 cycles (94° C. 30 sec., 55° C. 1 min., 72° C. 1 min.), 72° C. 7 min.]:

```
TGAP-F (XbaI_Xho):
                                        (SEQ ID NO: 5)
5'-tctagattgctcgagctatccaacaaactctag-3';
and TGAP-R (BamHI):
                                        (SEQ ID NO: 6)
5'-ggatcctctggtttagaagtagggactgtatg-3'.
```

EXAMPLE 2

Codon Optimization of araA, araB, and araD

Based on the data of Codon Usage Database (www.kazusa.or.jp/codon/index.html), codons of *Bacillus licheniformis* L-arabinose isomerase (araA), *Escherichia coli* L-ribulokinase (araB) and L-ribulose-5-phosphate 4-epimerase (araD) were replaced with the ones preferred by *Candida tropicalis*. As a result, CoAraA composed of the nucleotide sequence represented by SEQ ID NO: 7, CoAraB composed of the nucleotide sequence represented by SEQ ID NO: 8 and CoAraD composed of the nucleotide sequence represented by SEQ ID NO: 9 were synthesized (GENEART, Germany).

EXAMPLE 3

Figure 1:
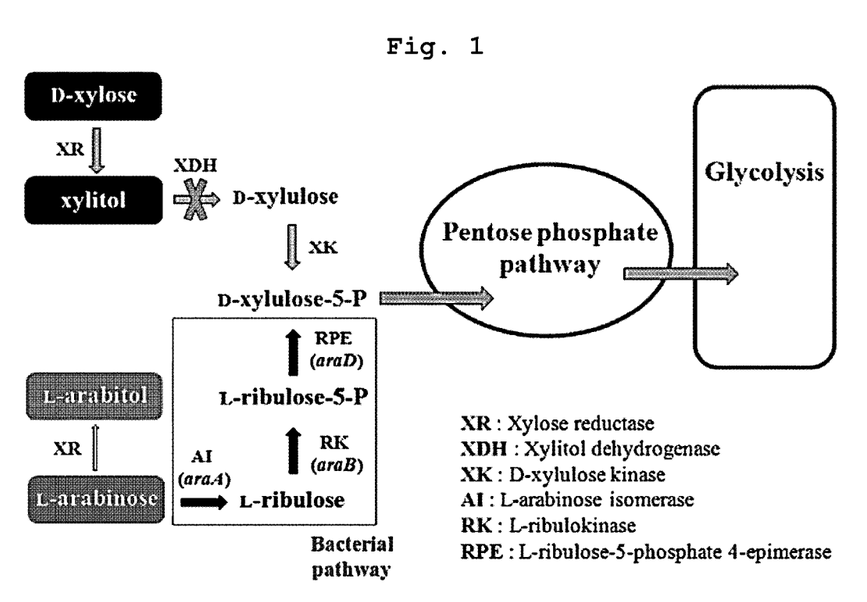
FIG. 1 is a diagram illustrating the metabolic pathway of xylose and arabinose in the xylitol producing microorganism.
Figure 2:
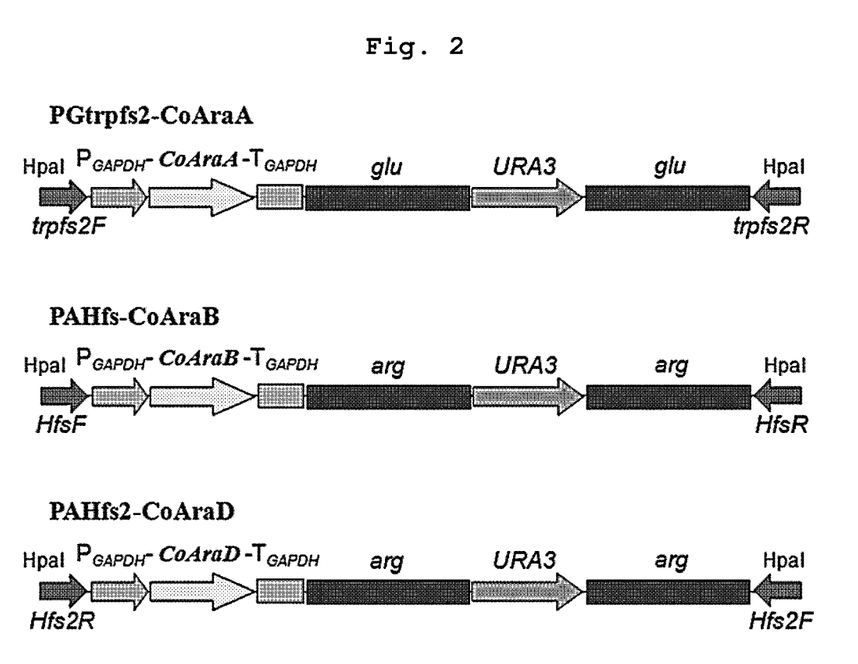
FIG. 2 is a diagram illustrating the genetic map of CoAraA, CoAraB and CoAraD expression cassettes.

Construction of CoAraA, CoAraB and CoAraD Expression Cassettes and Expression Strains The optimized genes synthesized in Example 2 were cloned in the cassette containing the promoter of glyceraldehyde-3-phosphate dehydrogenase and the repetitive sequence (glu or arg gene) for the elimination of selection marker. As a result, PGtrpfs2-CoAraA, PAHfs-CoAraB and PAHfs2-CoAraD were obtained (FIG. 2).

<3-1> Construction of Transformed *Candida tropicalis* in which Xylose Dehydrogenase Expression is Inhibited PCR was performed by using *Candida tropicalis* genomic DNA as a template with the below primers [94° C. 1 min., 25 cycles (94° C. 30 sec., 58° C. 30 sec., 72° C. 30 sec.), and 72° C. 3 min.] to amplify *Candida tropicalis* xylitol dehydrogenase gene. The amplified *Candida tropicalis* xylitol dehydrogenase gene was cloned into pGEM-T easy vector (BIONEX, Korea), followed by the introduction of BamHI site in the middle of the xylitol dehydrogenase gene. On the region of introduced BamHI, ura3 gene was introduced, resulting in the preparation of the transformation vector pXYL2-Ura3 (4.7 kb).

```
                              (SEQ ID NO: 10)
Primer F:    5'-aatggtcttgggtcacgaatcc-3'

(SEQ ID NO: 11)
Primer R:    5'-gctctgaccaagtcgtaggcttc-3'
```

The prepared vector pXYL2-Ura3 was introduced into *Candida tropicalis*, which was smeared on uracil-free solid selection medium [yeast nitrogen base (amino acid free) 6.7 g/L, glucose 20 g/L, and agarose powder 15 g/L], followed by incubation at 30° C. for 2 days. Then, the colonies formed on the solid medium were inoculated on the solid medium containing xylose [yeast nitrogen base (amino acid free) 6.7 g/L, xylose 20 g/L, and agarose powder 15 g/L] and the solid medium containing glucose [yeast nitrogen base (amino acid free) 6.7 g/L, glucose 20 g/L, and agarose powder 15 g/L] respectively, followed by incubation at 30° C. for 2 days. Strains that could not grow in the solid medium containing xylose but could grow on the solid medium containing glucose were selected. As a result, *Candida tropicalis* in which xylitol dehydrogenase was inactivated was obtained.

<3-2> Construction of Uracil Auxotroph of *Candida parapsilosis*

To use URA3 gene as the selection marker for strain construction, *Candida parapsilosis* was treated with methanesulfonic acid ethylester (EMS), the mutation inducing alkylating agent, leading to the construction of uracil auxotroph.

*Candida parapsilosis* was inoculated in 4 ml of YM medium (glucose 20 g/L, yeast extract 3 g/L, malt extract 3 g/L, and peptone 5 g/L), followed by shaking-culture at 150 rpm for 12 hours at 30° C. The culture solution was inoculated in 50 ml of YM medium, followed by shaking-culture at 200 rpm for 12 hours at 30° C., and then 30 ml of the culture solution was transferred into 50 ml tube, followed by washing twice with 30 ml of minimal A buffer ($K_2HPO_4$ 10.5 g/L, $KH_2PO_4$ 4.5 g/L, $(NH_4)_2SO_4$ 1.0 g/L and sodium citrate 0.5 g/L). The obtained cells were resuspended in 15 ml of minimal A buffer, to which 450 μl of EMS was added. While performing shaking-culture at 200 rpm at 30° C., reaction was induced for 90 minutes. The cells were washed twice with 5 ml of minimal A buffer, and then the obtained cells were resuspended in 1 ml of minimal A buffer. The cells were smeared on 5-FOA solid medium (yeast nitrogen base 6.7 g/L, glucose 20 g/L, 5-FOA 0.8 g/L, uracil 0.1 g/L, and agarose powder 15 g/L), followed by incubation for 2 days at 30° C. The colonies formed on the solid medium were the strains in which URA3 was inactivated, suggesting that uracil auxotroph of *Candida parapsilosis* was constructed.

<3-3> Construction of CoAraA, CoAraB and CoAraD Expressing Strain from Wild Type *Candida tropicalis*

The expression cassette PGtrpfs2-CoAraA constructed above was introduced into wild type *Candida tropicalis*, which was smeared on the uracil-free solid selection medium (yeast nitrogen base 6.7 g/L, glucose 20 g/L, and agarose powder 15 g/L), followed by incubation for 2 days at 30° C. The colonies formed on the solid medium were the strains introduced with the cassette. The colonies were inoculated in 4 ml of YM medium (glucose 20 g/L, yeast extract 3 g/L, malt extract 3 g/L, and peptone 5 g/L), followed by shaking-culture at 150 rpm for 12 hours at 30° C. Then, the culture solution was smeared on 5-FOA solid medium (yeast nitrogen base 6.7 g/L, glucose 20 g/L, 5-FOA 0.8 g/L, uracil 0.1 g/L, and agarose powder 15 g/L), followed by incubation for 2 days at 30° C.

The colonies formed on the solid medium were the strains in which the introduced URA3 gene was removed, and then PAHfs-CoAraB and PAHfs2-CoAraD were introduced therein stepwise, resulting in the construction of the transformant *Candida tropicalis* LBDAU expressing CoAraA, CoAraB, and CoAraD.

<3-4> Construction of CoAraA, CoAraB and CoAraD Expressing Strain from *Candida tropicalis* in which Xylitol Dehydrogenase is Removed The expression cassette PGtrpfs2-CoAraA constructed above was introduced into *Candida tropicalis* BSXDH-3 (Accession No: KCTC 11137BP) in which xylitol dehydrogenase was inactivated, which was smeared on the uracil-free solid selection medium (yeast nitrogen base 6.7 g/L, glucose 20 g/L, and agarose powder 15 g/L), followed by incubation for 2 days at 30° C. The colonies formed on the solid medium were the strains introduced with the cassette. The colonies were inoculated in 4 ml of YM medium (glucose 20 g/L, yeast extract 3 g/L, malt extract 3 g/L, and peptone 5 g/L), followed by shaking-culture at 150 rpm for 12 hours at 30° C. Then, the culture solution was smeared on 5-FOA solid medium (yeast nitrogen base 6.7 g/L, glucose 20 g/L, 5-FOA 0.8 g/L, uracil 0.1 g/L, and agarose powder 15 g/L), followed by incubation for 2 days at 30° C.

The colonies formed on the solid medium were the strains in which the introduced URA3 gene was removed, and then PAHfs-CoAraB and PAHfs2-CoAraD were introduced therein stepwise, resulting in the construction of the transformant *Candida tropicalis* PBDAU expressing CoAraA, CoAraB, and CoAraD.

<3-5> Construction of CoAraA, CoAraB and CoAraD Expressing Strain from *Candida parapsilosis*

The expression cassette PGtrpfs2-CoAraA constructed above was introduced into *Candida parapsilosis* in which URA3 was inactivated, which was smeared on the uracil-free solid selection medium (yeast nitrogen base 6.7 g/L, glucose 20 g/L, and agarose powder 15 g/L), followed by incubation for 2 days at 30° C. The colonies formed on the solid medium were the strains introduced with the cassette. The colonies were inoculated in 4 ml of YM medium (glucose 20 g/L, yeast extract 3 g/L, malt extract 3 g/L, and peptone 5 g/L), followed by shaking-culture at 150 rpm for 12 hours at 30° C. Then, the culture solution was smeared on 5-FOA solid medium (yeast nitrogen base 6.7 g/L, glucose 20 g/L, 5-FOA 0.8 g/L, uracil 0.1 g/L, and agarose powder 15 g/L), followed by incubation for 2 days at 30° C.

The colonies formed on the solid medium were the strains in which the introduced URA3 gene was removed, and then PAHfs-CoAraB and PAHfs2-CoAraD were introduced therein stepwise, resulting in the construction of the transformant *Candida parapsilosis* EBDAU expressing CoAraA, CoAraB, and CoAraD.

EXAMPLE 4

Confirmation of Operation of the Introduced Arabinose Metabolic Pathway

To confirm whether or not the arabinose metabolic pathway introduced in *Candida tropicalis* PBDAU, LBDAU and *Candida parapsilosis* EBDAU constructed in Example could be operating properly, the strains were cultured in arabinose minimal medium.

<4-1> Confirmation of Operation of the Arabinose Metabolic Pathway Introduced in Wild Type *Candida tropicalis* LBDAU LBDAU was inoculated in 4 ml of YM medium (glucose 20 g/L, yeast extract 3 g/L, malt extract 3 g/L and peptone 5 g/L), followed by shaking-culture at 150 rpm for 12 hours at 30° C. Then, the culture solution was inoculated in 50 ml of arabinose minimal medium (arabinose 20 g/L, yeast nitrogen base 6.7 g/L and agarose powder 15 g/L), followed by shaking-culture at 200 rpm for 60 hours at 30° C.

$OD_{600}$ was measured by using spectrophotometer, and the obtained value was presented by the pre-analyzed standard curve, by which dry cell weight over the time was measured. The concentrations of arabinose and arabitol were also measured over the time, and the measuring method is as follows. Samples were centrifuged and the supernatant was filtered with 0.2 μm. Then, the filtrate was analyzed with HPLC system [Sugar-Pak I column, HPLC pump, refractive index detector (Waters, USA), mobile phase: water, 0.5 ml/min, temperature: 90° C.].

TABLE 1

Cell growth, arabinose consumption and arabitol production in arabinose minimal medium

| | Wild-type | | | LBDAU | | |
|---|---|---|---|---|---|---|
| Time | Dry Cell Weight (g/L) | Arab-inose (g/L) | Arab-itol (g/L) | Dry Cell Weight (g/L) | Arab-inose (g/L) | Arab-itol (g/L) |
| 0 | 0 | 20 | 0 | 0 | 20 | 0 |
| 24 | 0 | 20 | 0 | 0.8 | 18.9 | 0 |
| 48 | 0 | 20 | 0 | 1.3 | 16.5 | 0 |
| 60 | 0 | 20 | 0 | 1.6 | 15.7 | 0 |

As a result, as shown in Table 1, the control wild type *Candida tropicalis* could not be growing in the minimal medium containing arabinose alone as a carbon source and thus neither arabinose therein was consumed nor arabitol was generated. On the other hand, LBDAU was growing as much as 1.6 g/L of dry cell weight with consuming 4.3 g/L of arabinose for 60 hours. Arabinose therein was not converted into arabitol and instead used all for cell metabolism.

Therefore, it was confirmed that the arabinose metabolic pathway introduced in LBDAU was successfully operated.

<4-2> Confirmation of Operation of the Arabinose Metabolic Pathway Introduced in the Transformant Strain *Candida tropicalis* PBDAU PBDAU was inoculated in 4 ml of YM medium (glucose 20 g/L, yeast extract 3 g/L, malt extract 3 g/L and peptone 5 g/L), followed by shaking-culture at 150 rpm for 12 hours at 30° C. Then, the culture solution was inoculated in 50 ml of arabinose minimal medium (arabinose 20 g/L, yeast nitrogen base 6.7 g/L and agarose powder 15 g/L), followed by shaking-culture at 200 rpm for 60 hours at 30° C.

$OD_{600}$ was measured by using spectrophotometer, and the obtained value was presented by the pre-analyzed standard curve, by which dry cell weight over the time was measured. The concentrations of arabinose and arabitol were also measured over the time, and the measuring method is as follows. Samples were centrifuged and the supernatant was filtered with 0.2 μm filter. Then, the filtrate was analyzed with HPLC system [Sugar-Pak I column, HPLC pump, refractive index detector (Waters, USA), mobile phase: water, 0.5 ml/min, temperature: 90° C.]. Dry cell weight, arabinose consumption and arabitol production over the time are as follows.

TABLE 2

Cell growth, arabinose consumption and arabitol production in arabinose minimal medium

| | BSXDH-3 | | | PBDAU | | |
|---|---|---|---|---|---|---|
| Time | Dry Cell Weight (g/L) | Arab-inose (g/L) | Arab-itol (g/L) | Dry Cell Weight (g/L) | Arab-inose (g/L) | Arab-itol (g/L) |
| 0 | 0 | 20 | 0 | 0 | 20 | 0 |
| 24 | 0 | 20 | 0 | 1.0 | 18.3 | 0 |
| 48 | 0 | 20 | 0 | 1.8 | 15.6 | 0 |
| 60 | 0 | 20 | 0 | 2.1 | 14.6 | 0 |

As a result, as shown in Table 2, the control BSXDH-3 could not be growing in the minimal medium containing arabinose alone as a carbon source and thus neither arabinose therein was consumed nor arabitol was generated. On the other hand, PBDAU was growing as much as 2.1 g/L of dry cell weight with consuming 5.4 g/L of arabinose for 60 hours. Arabinose therein was not converted into arabitol and instead used all for cell metabolism.

Therefore, it was confirmed that the arabinose metabolic pathway introduced in PBDAU was successfully operated.

<4-3> Confirmation of Operation of the Arabinose Metabolic Pathway Introduced in *Candida parapsilosis* EBDAU EBDAU was inoculated in 4 ml of YM medium (glucose 20 g/L, yeast extract 3 g/L, malt extract 3 g/L and peptone 5 g/L), followed by shaking-culture at 150 rpm for 12 hours at 30° C. Then, the culture solution was inoculated in 50 ml of arabinose minimal medium (arabinose 20 g/L, yeast nitrogen base 6.7 g/L and agarose powder 15 g/L), followed by shaking-culture at 200 rpm for 60 hours at 30° C.

$OD_{600}$ 20 was measured by using spectrophotometer, and the obtained value was presented by the pre-analyzed standard curve, by which dry cell weight over the time was measured. The concentrations of arabinose and arabitol were also measured over the time, and the measuring method is as follows. Samples were centrifuged and the supernatant was filtered with 0.2 μm filter. Then, the filtrate was analyzed with HPLC system [Sugar-Pak I column, HPLC pump, refractive index detector (Waters, USA), mobile phase: water, 0.5 ml/min, temperature: 90° C.]. Dry cell weight, arabinose consumption and arabitol production over the time are as follows.

TABLE 3

Cell growth, arabinose consumption and arabitol production in arabinose minimal medium

| | Wild-type | | | EBDAU | | |
|---|---|---|---|---|---|---|
| Time | Dry Cell Weight (g/L) | Arabinose (g/L) | Arabitol (g/L) | Dry Cell Weight (g/L) | Arabinose (g/L) | Arabitol (g/L) |
| 0 | 0 | 20 | 0 | 0 | 20 | 0 |
| 24 | 0 | 20 | 0 | 0.9 | 19.0 | 0 |
| 48 | 0 | 20 | 0 | 1.2 | 17.1 | 0 |
| 60 | 0 | 20 | 0 | 1.4 | 15.9 | 0 |

As a result, as shown in Table 3, the control wild-type *Candida parapsilosis* could not be growing in the minimal medium containing arabinose alone as a carbon source and thus neither arabinose therein was consumed nor arabitol was generated. On the other hand, EBDAU was growing as much as 1.4 g/L of dry cell weight with consuming 4.1 g/L of arabinose for 60 hours. Arabinose therein was not converted into arabitol and instead used all for cell metabolism.

Therefore, it was confirmed that the arabinose metabolic pathway introduced in EBDAU was successfully operated.

EXAMPLE 5

Production of Xylitol by Using Transformants

<5-1> Production of Xylitol by Using the Transformant PBDAU and Glucose as a Cosubstrate The constructed transformant PBDAU was inoculated in 4 ml of YM medium (glucose 20 g/L, yeast extract 3 g/L, malt extract 3 g/L, and peptone 5 g/L), followed by shaking-culture at 150 rpm for 12 hours at 30° C. Then, the culture solution was inoculated in 50 ml of production medium containing xylose, arabinose and glucose (xylose 30 g/L, arabinose 30 g/L, glucose 20 g/L, yeast extract 10 g/L, $KH_2PO_4$ 5 g/L and $MgSO_4 7H_2O$ 0.2 g/L), followed by shaking-culture at 200 rpm for 60 hours at 30° C. Glucose was added thereto at the concentration of 2.5 g/L each 14 hours, 20 hours, 26 hours, and 32 hours after the culture began.

The concentrations of xylose, xylitol, arabinose and arabitol were measured over the time, and the measuring method is as follows. Samples were centrifuged and the supernatant was filtered with 0.2 μm filter. Then, the filtrate was analyzed with HPLC system [Sugar-Pak I column, HPLC pump, refractive index detector (Waters, USA), mobile phase: water, 0.5 ml/min, temperature: 90° C.]. The concentrations of xylose, xylitol, arabinose and arabitol over the time are as follows.

TABLE 4

Concentrations of xylitol and arabitol over the time

| | BSXDH-3 | | | | PBDAU | | | |
|---|---|---|---|---|---|---|---|---|
| Time | Xylose (g/L) | Xylitol (g/L) | Arabinose (g/L) | Arabitol (g/L) | Xylose (g/L) | Xylitol (g/L) | Arabinose (g/L) | Arabitol (g/L) |
| 0 | 27.3 | 0 | 28.3 | 0 | 27.3 | 0 | 28.3 | 0 |
| 6 | 26.6 | 0 | 28.0 | 0 | 26.7 | 0 | 28.1 | 0 |
| 12 | 22.8 | 3.2 | 27.9 | 0 | 22.7 | 3.6 | 28.0 | 0 |
| 24 | 11.7 | 14.1 | 25.4 | 1.7 | 6.8 | 20.1 | 24.7 | 0 |
| 36 | 4.0 | 22.4 | 22.7 | 4.2 | 1.0 | 25.5 | 21.2 | 0 |
| 42 | 1.2 | 25.3 | 20.9 | 6.0 | 0 | 26.8 | 20.2 | 0 |
| 48 | 0 | 26.5 | 18.5 | 8.3 | 0 | 27.0 | 18.5 | 0 |
| 60 | 0 | 27.1 | 15.6 | 11.4 | 0 | 27.0 | 17.9 | 0 |

As a result, xylitol productivity of BSXDH-3 was 0.55 g/L/h, and xylitol productivity of PBDAU was 0.63 g/L/h, suggesting that PBDAU demonstrated 15% higher xylitol productivity than that of the control BSXDH-3. In the meantime, BSXDH-3 produced 11.4 g/L of arabitol for 60 hours, while PBDAU did not produce arabitol, the byproduct, and produced xylitol only.

Therefore, the production method of xylitol using PBDAU of the present invention was confirmed to increase xylitol production yield significantly by inhibiting the generation of arabitol interrupting the purification and crystallization of xylitol.

<5-2> Production of Xylitol by Using the Transformant PBDAU and Glycerol as a Cosubstrate The constructed transformant PBDAU was inoculated in 4 ml of YM medium (glucose 20 g/L, yeast extract 3 g/L, malt extract 3 g/L, and peptone 5 g/L), followed by shaking-culture at 150 rpm for 12 hours at 30° C. Then, the culture solution was inoculated in 50 ml of production medium containing xylose, arabinose and glycerol (xylose 30 g/L, arabinose 30 g/L, glycerol 20 g/L, yeast extract 10 g/L, $KH_2PO_4$ 5 g/L and $MgSO_4 7H_2O$ 0.2 g/L), followed by shaking-culture at 200 rpm for 36 hours at 30° C.

The concentrations of xylose, xylitol, arabinose and arabitol were measured over the time, and the measuring method is as follows. Samples were centrifuged and the supernatant was filtered with 0.2 μm filter. Then, the filtrate was analyzed with HPLC system [Sugar-Pak I column, HPLC pump, refractive index detector (Waters, USA), mobile phase: water, 0.5 ml/min, temperature: 90° C.]. The concentrations of xylose, xylitol, arabinose and arabitol over the time are as follows.

TABLE 5

Concentrations of xylitol and arabitol over the time

| | BSXDH-3 | | | | PBDAU | | | |
|---|---|---|---|---|---|---|---|---|
| Time | Xylose (g/L) | Xylitol (g/L) | Arabinose (g/L) | Arabitol (g/L) | Xylose (g/L) | Xylitol (g/L) | Arabinose (g/L) | Arabitol (g/L) |
| 0 | 28.3 | 0 | 27.8 | 0 | 28.3 | 0 | 27.8 | 0 |
| 12 | 25.2 | 2.5 | 27.0 | 0 | 24.7 | 3.4 | 26.4 | 0 |
| 24 | 13.0 | 15.1 | 24.7 | 2.0 | 9.0 | 19.8 | 25.6 | 0 |
| 36 | 3.5 | 25.0 | 22.6 | 4.2 | 0.8 | 26.7 | 24.8 | 0 |
| 42 | 0 | 27.3 | 20.3 | 6.4 | 0 | 27.1 | 24.1 | 0 |

As a result, xylitol productivity of BSXDH-3 was 0.65 g/L/h, and xylitol productivity of PBDAU was 0.74 g/L/h, suggesting that PBDAU demonstrated 14% higher xylitol productivity than that of the control BSXDH-3. In the meantime, BSXDH-3 produced 6.4 g/L of arabitol for 42 hours, while PBDAU did not produce arabitol, the byproduct, and produced xylitol only.

Therefore, the production method of xylitol using PBDAU of the present invention was confirmed to increase xylitol production yield significantly by inhibiting the generation of arabitol interrupting the purification and crystallization of xylitol.

<5-3> Production of Xylitol by Using the Transformant LBDAU and Glucose as a Cosubstrate The constructed transformant LBDAU was inoculated in 4 ml of YM medium (glucose 20 g/L, yeast extract 3 g/L, malt extract 3 g/L, and peptone 5 g/L), followed by shaking-culture at 150 rpm for 12 hours at 30° C. Then, the culture solution was inoculated in 50 ml of production medium containing xylose, arabinose and glucose (xylose 30 g/L, arabinose 30 g/L, glucose 20 g/L, yeast extract 10 g/L, $KH_2PO_4$ 5 g/L and MgSO$_4$7H$_2$O 0.2 g/L), followed by shaking-culture at 200 rpm for 60 hours at 30° C. Glucose was added thereto at the concentration of 2.5 g/L each 14 hours, 20 hours, 26 hours, and 32 hours after the culture began.

The concentrations of xylose, xylitol, arabinose and arabitol were measured over the time, and the measuring method is as follows. Samples were centrifuged and the supernatant was filtered with 0.2 μm filter. Then, the filtrate was analyzed with HPLC system [Sugar-Pak I column, HPLC pump, refractive index detector (Waters, USA), mobile phase: water, 0.5 ml/min, temperature: 90° C.]. The concentrations of xylose, xylitol, arabinose and arabitol over the time are as follows.

TABLE 6

Concentrations of xylitol and arabitol over the time

| | Wild-type | | | | LBDAU | | | |
|---|---|---|---|---|---|---|---|---|
| Time | Xy-lose (g/L) | Xyli-tol (g/L) | Arab-inose (g/L) | Arab-itol (g/L) | Xy-lose (g/L) | Xyli-tol (g/L) | Arab-inose (g/L) | Arab-itol (g/L) |
| 0 | 27.5 | 0 | 28.0 | 0 | 27.5 | 0 | 28.0 | 0 |
| 6 | 26.9 | 0 | 28.0 | 0 | 27.0 | 0 | 28.0 | 0 |
| 12 | 24.0 | 2.0 | 27.5 | 0 | 23.5 | 2.7 | 27.7 | 0 |
| 24 | 12.0 | 12.3 | 26.3 | 1.0 | 11.4 | 17.0 | 25.2 | 0 |
| 36 | 3.3 | 18.5 | 23.2 | 3.8 | 2.6 | 21.3 | 21.5 | 0 |
| 42 | 1.1 | 19.1 | 21.0 | 5.7 | 1.0 | 22.0 | 19.8 | 0 |
| 48 | 0 | 19.4 | 19.2 | 7.7 | 0 | 22.3 | 18.6 | 0 |
| 60 | 0 | 19.4 | 16.0 | 10.3 | 0 | 22.3 | 16.9 | 0 |

As a result, xylitol productivity of the wild-type strain was 0.51 g/L/h, and xylitol productivity of LBDAU was 0.59 g/L/h, suggesting that LBDAU demonstrated 15% higher xylitol productivity than that of the wild-type strain. In the meantime, the wild-type strain produced 10.3 g/L of arabitol for 60 hours, while LBDAU did not produce arabitol, the byproduct, and produced xylitol only.

<5-4> Production of Xylitol by Using the Transformant LBDAU and Glycerol as a Cosubstrate The constructed transformant LBDAU was inoculated in 4 ml of YM medium (glucose 20 g/L, yeast extract 3 g/L, malt extract 3 g/L, and peptone 5 g/L), followed by shaking-culture at 150 rpm for 12 hours at 30° C. Then, the culture solution was inoculated in 50 ml of production medium containing xylose, arabinose and glycerol (xylose 30 g/L, arabinose 30 g/L, glycerol 20 g/L, yeast extract 10 g/L, KH$_2$PO$_4$ 5 g/L and MgSO$_4$7H$_2$O 0.2 g/L), followed by shaking-culture at 200 rpm for 36 hours at 30° C.

The concentrations of xylose, xylitol, arabinose and arabitol were measured over the time, and the measuring method is as follows. Samples were centrifuged and the supernatant was filtered with 0.2 μm filter. Then, the filtrate was analyzed with HPLC system [Sugar-Pak I column, HPLC pump, refractive index detector (Waters, USA), mobile phase: water, 0.5 ml/min, temperature: 90° C.]. The concentrations of xylose, xylitol, arabinose and arabitol over the time are as follows.

TABLE 7

Concentrations of xylitol and arabitol over the time

| | Wild-type | | | | LBDAU | | | |
|---|---|---|---|---|---|---|---|---|
| Time | Xy-lose (g/L) | Xyli-tol (g/L) | Arab-inose (g/L) | Arab-itol (g/L) | Xy-lose (g/L) | Xyli-tol (g/L) | Arab-inose (g/L) | Arab-itol (g/L) |
| 0 | 28.5 | 0 | 27.7 | 0 | 28.5 | 0 | 27.7 | 0 |
| 12 | 23.6 | 2.3 | 27.5 | 0 | 23.8 | 3.8 | 27.7 | 0 |
| 24 | 11.5 | 13.5 | 24.8 | 1.7 | 10.2 | 17.6 | 26.9 | 0 |
| 36 | 1.8 | 20.7 | 22.5 | 4.3 | 1.0 | 22.7 | 25.1 | 0 |
| 42 | 0 | 20.9 | 20.5 | 6.7 | 0 | 23.0 | 23.9 | 0 |

As a result, xylitol productivity of the wild-type strain was 0.58 g/L/h, and xylitol productivity of LBDAU was 0.63 g/L/h, suggesting that LBDAU demonstrated 10% higher xylitol productivity than that of the control wild-type strain. In the meantime, the wild-type strain produced 6.7 g/L of arabitol for 42 hours, while LBDAU did not produce arabitol, the byproduct, and produced xylitol only.

<5-5> Production of Xylitol by Using the Transformant EBDAU and Glucose as a Cosubstrate The constructed transformant EBDAU was inoculated in 4 ml of YM medium (glucose 20 g/L, yeast extract 3 g/L, malt extract 3 g/L, and peptone 5 g/L), followed by shaking-culture at 150 rpm for 12 hours at 30° C. Then, the culture solution was inoculated in 50 ml of production medium containing xylose, arabinose and glucose (xylose 30 g/L, arabinose 30 g/L, glucose 20 g/L, yeast extract 10 g/L, KH$_2$PO$_4$ 5 g/L and MgSO$_4$7H$_2$O 0.2 g/L), followed by shaking-culture at 200 rpm for 60 hours at 300. Glucose was added thereto at the concentration of 2.5 g/L each 14 hours, 20 hours, 26 hours, and 32 hours after the culture began.

The concentrations of xylose, xylitol, arabinose and arabitol were measured over the time, and the measuring method is as follows. Samples were centrifuged and the supernatant was filtered with 0.2 μm filter. Then, the filtrate was analyzed with HPLC system [Sugar-Pak I column, HPLC pump, refractive index detector (Waters, USA), mobile phase: water, 0.5 ml/min, temperature: 90° C.]. The concentrations of xylose, xylitol, arabinose and arabitol over the time are as follows.

TABLE 8

Concentrations of xylitol and arabitol over the time

| | Wild-type | | | | EBDAU | | | |
|---|---|---|---|---|---|---|---|---|
| Time | Xy-lose (g/L) | Xyli-tol (g/L) | Arab-inose (g/L) | Arab-itol (g/L) | Xy-lose (g/L) | Xyli-tol (g/L) | Arab-inose (g/L) | Arab-itol (g/L) |
| 0 | 27.7 | 0 | 27.8 | 0 | 27.7 | 0 | 27.8 | 0 |
| 6 | 27.0 | 0 | 27.8 | 0 | 27.5 | 0 | 27.8 | 0 |
| 12 | 24.0 | 2.1 | 27.5 | 0 | 24.1 | 2.5 | 27.2 | 0 |
| 24 | 13.5 | 11.1 | 26.6 | 0.8 | 11.1 | 14.5 | 26.5 | 0 |
| 36 | 4.9 | 16.4 | 23.5 | 3.5 | 3.5 | 19.7 | 22.9 | 0 |
| 42 | 2.5 | 18.5 | 21.4 | 5.5 | 1.0 | 20.7 | 21.3 | 0 |
| 48 | 1 | 18.4 | 18.8 | 7.3 | 0 | 20.7 | 18.9 | 0 |
| 60 | 0 | 18.4 | 17.5 | 9.8 | 0 | 20.5 | 17.8 | 0 | a result, xylitol productivity of the wild-type strain was 0.44 g/L/h, and xylitol productivity of EBDAU was 0.49 g/L/h, suggesting that EBDAU demonstrated 12% higher xylitol productivity than that of the wild-type strain. In the meantime, the wild-type strain produced 9.8 g/L of arabitol for 60 hours, while EBDAU did not produce arabitol, the byproduct, and produced xylitol only.

Therefore, the production method of xylitol using EBDAU of the present invention was confirmed to increase xylitol production yield significantly by inhibiting the generation of arabitol interrupting the purification and crystallization of xylitol.

<5-6> Production of Xylitol by Using the Transformant EBDAU and Glycerol as a Cosubstrate The constructed transformant EBDAU was inoculated in 4 ml of YM medium (glucose 20 g/L, yeast extract 3 g/L, malt extract 3 g/L, and peptone 5 g/L), followed by shaking-culture at 150 rpm for 12 hours at 30° C. Then, the culture solution was inoculated in 50 ml of production medium containing xylose, arabinose and glycerol (xylose 30 g/L, arabinose 30 g/L, glycerol 20 g/L, yeast extract 10 g/L, $KH_2PO_4$ 5 g/L and $MgSO_4 7H_2O$ 0.2 g/L), followed by shaking-culture at 200 rpm for 36 hours at 30° C.

The concentrations of xylose, xylitol, arabinose and arabitol were measured over the time, and the measuring method is as follows. Samples were centrifuged and the supernatant was filtered with 0.2 μm filter. Then, the filtrate was analyzed with HPLC system [Sugar-Pak I column, HPLC pump, refractive index detector (Waters, USA), mobile phase: water, 0.5 ml/min, temperature: 90° C.]. The concentrations of xylose, xylitol, arabinose and arabitol over the time are as follows.

TABLE 9

Concentrations of xylitol and arabitol over the time

| | Wild-type | | | | LBDAU | | | |
|---|---|---|---|---|---|---|---|---|
| Time | Xylose (g/L) | Xylitol (g/L) | Arabinose (g/L) | Arabitol (g/L) | Xylose (g/L) | Xylitol (g/L) | Arabinose (g/L) | Arabitol (g/L) |
| 0 | 28.0 | 0 | 27.5 | 0 | 28.0 | 0 | 27.5 | 0 |
| 12 | 26.5 | 1.3 | 27.5 | 0 | 24.3 | 3.2 | 27.6 | 0 |
| 24 | 13.5 | 11.9 | 24.6 | 1.5 | 11.8 | 16.6 | 24.2 | 0 |
| 36 | 2.8 | 17.8 | 22.5 | 3.9 | 2.5 | 20.2 | 23.1 | 0 |
| 42 | 0 | 20.1 | 21.1 | 5.2 | 0 | 21.0 | 23.0 | 0 |

As a result, xylitol productivity of the wild-type strain was 0.49 g/L/h, and xylitol productivity of EBDAU was 0.56 g/L/h, suggesting that EBDAU demonstrated 13% higher xylitol productivity than that of the wild-type strain. In the meantime, the wild-type strain produced 5.2 g/L of arabitol for 42 hours, while EBDAU did not produce arabitol, the byproduct, and produced xylitol only.

Therefore, the production method of xylitol using EBDAU of the present invention was confirmed to increase xylitol production yield significantly by inhibiting the generation of arabitol interrupting the purification and crystallization of xylitol.

EXAMPLE 6

Mass Production of Xylitol by Using the Transformant PBDAU and Biomass Hydrolysate To produce xylitol at a large scale by using the transformant, corncob hydrolysate (xylose 82.9%, arabinose 11.4%, and glucose 5.7%) was used as a substrate and glycerol was used as a cosubstrate. The biomass of corncob, sugar cane stalk, coconut byproduct and birch are rich in hemicelluloses composed of xylose, arabinose and glucose. In particular, the content of xylose is especially high. Therefore, the biomass hydrolysate can be directly used for the production of xylitol.

The constructed transformant PBDAU was inoculated in 50 ml of YM medium (glucose 20 g/L, yeast extract 3 g/L, malt extract 3 g/L, and peptone 5 g/L), followed by shaking-culture at 200 rpm for 12 hours at 30° C. Then, the culture solution was inoculated in a fermenter containing 1 L of xylitol production medium prepared by using biomass hydrolysate (xylose 50 g/L, glucose 3.5 g/L, arabinose 6.9 g/L, glycerol 15 g/L, yeast extract 10 g/L, $KH_2PO_4$ 5 g/L and $MgSO_4 7H_2O$ 0.2 g/L), followed by shaking-culture (30° C., pH4.0, 500-800 rpm). After 12 hours from the culture began, feeding solution (xylose 503 g/L, glucose 34.7 g/L, arabinose 69.2 g/L, and glycerol 150 g/L) was added to the medium to regulate the concentration of xylose under 100 g/L, followed by fed-batch culture for 72 hours.

$OD_{600}$ was measured by using spectrophotometer, and the obtained value was presented by the pre-analyzed standard curve, by which dry cell weight over the time was measured. The concentrations of xylose, xylitol, arabinose and arabitol were also measured over the time, and the measuring method is as follows. Samples were centrifuged and the supernatant was filtered with 0.2 μm filter. Then, the filtrate was analyzed with HPLC system [Sugar-Pak I column, HPLC pump, refractive index detector (Waters, USA), mobile phase: water, 0.5 ml/min, temperature: 90° C.]. Dry cell weight and the concentrations of xylose, xylitol, arabinose and arabitol over the time are as follows.

TABLE 10

Concentrations of xylitol and arabitol over the time

| | BSXDH-3 | | | | | PBDAU | | | | |
|---|---|---|---|---|---|---|---|---|---|---|
| Time | Dry Cell Weight (g/L) | Xylose (g/L) | Xylitol (g/L) | Arabinose (g/L) | Arabitol (g/L) | Dry Cell Weight (g/L) | Xylose (g/L) | Xylitol (g/L) | Arabinose (g/L) | Arabitol (g/L) |
| 0 | 0.2 | 53.7 | 0 | 7.0 | 0 | 0.3 | 50.7 | 0 | 7.0 | 0 |
| 12 | 15.9 | 37.5 | 10.6 | 6.7 | 0 | 16.2 | 32.1 | 16.0 | 6.3 | 0 |
| 24 | 21.3 | 67.3 | 41.5 | 15.4 | 0 | 23.4 | 58.1 | 52.6 | 14.5 | 0 |
| 36 | 25.2 | 78.9 | 63.4 | 19.9 | 0 | 27.4 | 69.8 | 76.7 | 19.4 | 0 |
| 48 | 28.3 | 58.3 | 90.3 | 19.2 | 2.2 | 28.3 | 49.2 | 100.5 | 17.9 | 0 |
| 60 | 30.2 | 23.8 | 127.9 | 17.6 | 3.1 | 31.8 | 19.6 | 132.9 | 16.9 | 0 |
| 72 | 31.2 | 2.5 | 155.6 | 12.9 | 6.4 | 31.0 | 2.6 | 163.7 | 13.0 | 0 |

As a result, xylitol productivity of BSXDH-3 was 2.16 g/L/h, and xylitol productivity of PBDAU was 2.28 g/L/h, suggesting that PBDAU demonstrated 5.6% higher xylitol productivity than that of the control BSXDH-3. In the meantime, BSXDH-3 produced 6.4 g/L of arabitol for 72 hours, while PBDAU did not produce arabitol, the byproduct, and produced xylitol only.

Therefore, the PBDAU strain of the present invention was confirmed to produce xylitol with high concentration and high productivity but not to produce arabitol, the byproduct, during the mass-production of xylitol using the real biomass hydrolysate.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

Deposits

The following microorganisms were deposited with the Korean Collection for Type Cultures (KCTC), Korea Research Institute of Bioscience and Biotechnology (KRIBB), 111 Gwahangno, Yuseong-gu, Daejeon 305-806, Republic of Korea, under the terms of the Budapest Treaty on the International Recognition of the Deposit of Microorganisms for the Purpose of Patent Procedure:

*Candida tropicalis* BSXDH, Accession Number KCTC 11137BP, deposited Jun. 19, 2007; and

*Candidia tropicalis* PBDAU, Accession Number KCTC 11761BP, deposited Sep. 8, 2010.

What is claimed is:

1. An isolated microorganism of the genus *Candida*, wherein said microorganism is obtained by genetic modification from a starting microorganism such that arabitol production is inhibited and xylitol production is increased compared to said starting microorganism, wherein said microorganism comprises gene expression cassettes of the following 1)-3):
   1) a gene expression cassette comprising a promoter operably linked to a polynucleotide encoding L-arabinose isomerase operably linked to a terminator;
   2) a gene expression cassette comprising a promoter operably linked to a polynucleotide encoding L-ribulokinase operably linked to a terminator; and
   3) a gene expression cassette comprising a promoter operably linked to a polynucleotide encoding L-ribulose-5-phosphate 4-epimerase operably linked to a terminator.

2. The isolated microorganism of the genus *Candida* according to claim 1, wherein the microorganism of genus *Candida* is selected from the group consisting of *Candida guillermondi* (*C. guillermondi*), *Candida parapsilosis* (*C. parapsilosis*) and *Candida tropicalis* (*C. tropicalis*).

3. The isolated microorganism of the genus *Candida* according to claim 2, wherein the *Candida tropicalis* comprises inactivated xylitol dehydrogenase.

4. The isolated microorganism of the genus *Candida* according to claim 3, wherein the *Candida tropicalis* is deposited under Accession No: KCTC 11137BP.

5. The isolated microorganism of the genus *Candida* according to claim 1, wherein the isolated microorganism is deposited under Accession No: KCTC 11761BP.

6. A method for producing the isolated microorganism of the genus *Candida* of claim 1, said method comprising the step of introducing the gene expression cassettes of 1)-3) into a microorganism of the genus *Candida*.

7. The method according to claim 6, wherein the microorganism of genus *Candida* is selected from the group consisting of *Candida guillermondi, Candida parapsilosis* and *Candida tropicalis*.

8. The production method according to claim 7, wherein the *Candida tropicalis* comprises inactivated xylitol dehydrogenase.

9. The method according to claim 8, wherein the *Candida tropicalis* is deposited under Accession No: KCTC 11137BP.

10. The method according to claim 6, wherein the isolated microorganism is deposited under Accession No: KCTC 11761BP.

11. A mass-production method of producing xylitol comprising the following steps:
    1) culturing the isolated microorganism of the genus *Candida* of claim 1 in medium containing biomass hydrolysate and a carbon source;
    2) producing xylitol from the cultured microorganism; and
    3) separating xylitol from the culture solution.

12. The mass-production method of producing xylitol according to claim 11, wherein the biomass hydrolysate of step 1) is selected from the group consisting of corncob hydrolysate, sugar cane hydrolysate, coconut byproduct and birch hydrolysate.

13. The mass-production method of producing xylitol according to claim 11, wherein the carbon source of step 1) is selected from the group consisting of glucose, glycerol, molasses, hydrol, sucrose, mannose, maltose, cellobiose and a mixture thereof.

* * * * *

SEQUENCE LISTING

```
<160> NUMBER OF SEQ ID NOS: 11

<210> SEQ ID NO 1
<211> LENGTH: 1455
<212> TYPE: DNA
<213> ORGANISM: Artificial Sequence
<220> FEATURE:
<223> OTHER INFORMATION: promoter

<400> SEQUENCE: 1
aacgtggtat ggttgtaaga aacatattgc aactggagat agcgatcgtt caatttattc      60
cgattttgtg ggggaagtcg cccgctggtg ggcgtgcgcg aatggcaaaa gaaactcgac     120
catgcttttc atcatccctt aacagagcaa tcatatttta aacgttcaag caaaaagaaa     180
cgttggtttc ggctaatgat cacctgaaag gcaaaatcct tccatgtatg aacatgtagg     240
ttattccttt tttttgcaac accctcgggc agttgttcat attcccggaa aacaccacca     300
ctcggggcta agtggaagtt ctacaatccc ggggaaataa ggagccccgg tgagcacgcg     360
cacacaccac cttcacttca ttttgtccga gggaagcagc acgtgaagtc ggaacacgag     420
aggagcattt cttctatttt tttcttctct actgtgagtg catgattata tatgtaatca     480
aaagcgatca acttatggta gggtcgtgca cggcgcaccg ggttccaaaa tgatctgtga     540
gggacaaaat tctttttttt ttccagcatg ccgctggtgg caaataccgt ggtggtatga     600
tgcaccctat gccattgatt cacaccacca ccattaatca acaattgaga gaggacaaaa     660
gtgaactatt ggtggtcgtc aggttatact cgtcagcttc ggaatattac gtcccttcag     720
tttgtgaaat gtcatcctgg cgatgttcga gagagatcag tccgagagcg cgtggtagga     780
gaaacggagc actgcagcaa caaaaaaaaa atccaaaccc aggggggagg aagaagaaca     840
gccagggaaa ttgttcaccg acctgaccgt aaatttgctg ctgaaagaaa cgtgtcaaac     900
aagaccaatt ggctcaattg accctgaggg agtactttgt ctgccaccaa tgcttccacc     960
aaaacgctac ttttgttttg caatcggatg gtgtgggtct ggggtccacc tgttttgtta    1020
agctacagaa ggtggcatat tcctctgatc aggtgctttt tttcggctgc tgctgctcgt    1080
ggtggtgtag tggtagtggt gtgtgtgcgt gtgcgtgagg gaggccgctt tttgctctct    1140
gactcctccc aatcagaagt tgctgtagca gtgaaacaac acaatggatg ataatgcccc    1200
gggcggtgcg tgtccgacac aaaccactac atttttttagc tgggagcata ctgccactac    1260
gacccaccca cccatggtca acaaaaaaat tctgacaaat tataaaataa cccttggatt    1320
cccccttgga aaaattttttg gtatttctct ctttcttttc cttttccttt ccctcttctt    1380
tttccctcca tcaatcaatt gacgttcagt aactcaatta attacatcac atccctcaat    1440
taaagaattt aaaca                                                     1455
```

<210> SEQ ID NO 2
<211> LENGTH: 309
<212> TYPE: DNA
<213> ORGANISM: Artificial Sequence
<220> FEATURE:
<223> OTHER INFORMATION: teminator

<400> SEQUENCE: 2

```
ctatccaaca aactctaggg gttgtgcttt ttgaaaaaaa catataggtt ttattgaaat     60
agccacaatg tctgttgaga ggacatttga tttgttttat attatcgtat atgtaccctg    120
gaatatattg cgttttttaa caaaagacaa acaacggtct ttagtttttt tttcaatcaa    180
tcaatgttcg tgatcgtaga gagaaggaga aaaaaagagt aaacataaac aaacatcttt    240
cttttttacaa acgagtacaa gcaacagcca tgtcacaaga tgccatacag tccctacttc    300
taaaccaga                                                            309
```

<210> SEQ ID NO 3
<211> LENGTH: 29
<212> TYPE: DNA
<213> ORGANISM: Artificial Sequence
<220> FEATURE:
<223> OTHER INFORMATION: PGAP forward primer

<400> SEQUENCE: 3

```
agatctaacg tggtatggtt gtaagaaac                                       29
```

<210> SEQ ID NO 4
<211> LENGTH: 34
<212> TYPE: DNA
<213> ORGANISM: Artificial Sequence
<220> FEATURE:
<223> OTHER INFORMATION: PGAP reverse primer

<400> SEQUENCE: 4

```
ggatccgcgt ctagatgttt aaattcttta attg                                 34
```

<210> SEQ ID NO 5
<211> LENGTH: 33
<212> TYPE: DNA
<213> ORGANISM: Artificial Sequence
<220> FEATURE:
<223> OTHER INFORMATION: TGAP forward primer

<400> SEQUENCE: 5

```
tctagattgc tcgagctatc caacaaactc tag                                  33
```

<210> SEQ ID NO 6
<211> LENGTH: 32
<212> TYPE: DNA
<213> ORGANISM: Artificial Sequence
<220> FEATURE:
<223> OTHER INFORMATION: TGAP reverse primer

<400> SEQUENCE: 6

```
ggatcctctg gtttagaagt agggactgta tg                                   32
```

<210> SEQ ID NO 7
<211> LENGTH: 1425
<212> TYPE: DNA
<213> ORGANISM: Bacillus licheniformis

<400> SEQUENCE: 7

```
atgttgacca ccggtaagaa agaattctgg ttcgttgttg gttcccaaca cttgtacggt     60
```

-continued

```
gaagaaacct tggctgaagt tagagcccac gctcaagcta tgaccgatgc tttgaacgaa      120
tccgctgttt tgccataccc attggtcttg caagatttgg ctgtcaacgc tgataagatt      180
acctccatta tgaaggaagt caactacaga gatgaagttg ctggtgttat tacctggatg      240
cacaccttct caccagctaa gatgtggatt agaggtacta agttgttgca aaagccattg      300
ttgcacttgg ctacccaatt caacgaatcc attccatggc caaccattga tatggatttc      360
atgaacttga atcaatccgc tcacggtgat agagaatacg gtttcattaa cgccagattg      420
aagaagcaaa acaaggttgt tgtcggttac tgggaaagac cagaagttca acaacaaatt      480
gctgaatgga tggatgttgc tgttgcttac aacgaatcct tcaacattaa ggttgctaga      540
ttcggtgaca acatgagaaa cgttgctgtt accgaaggtg ataagattga agctcaaatt      600
caattcggtt ggaccgttga ttacttcggt attggtgatt tggtccaata cgtcaacgct      660
gttaccgatg aagaaatcaa cagattgttc gctgaatacg ctgacttgta cgaattcgat      720
tacggtactt actccagaga agattgggaa aagtccgtta aggttcaagc ttcctacgaa      780
attgccatca agagattctt ggatgatggt ggttacaacg cttttcaccac caacttcgaa      840 gatttgtacg gtatgaagca attgccaggt ttggctgttc aaagattgat ggctcaaggt      900
tacggtttcg ctggtgaagg tgattggaaa accgctgctt ggatagatt gttgaaggtt      960 atgtccagaa atcaatccac cggtttcatg aagattaca cctacgaatt ggctgctggt     1020
caagaatcca tcttgcaatc ccacatgttg aagttgatc catccttggc ttccaacaag     1080
ccaaagatta tcgtttcccc attgggtatt ggtgacagag aagatccagc tagattggtt     1140
ttcgatggta aggctggtga tggtgttgtt gtttccatgg ctgatttcgg tactcactac     1200
aagttgttga tcaacgaagt ttccgctttc gaaccaaccg ttccagctcc aaacttgcca     1260
gttgctagag ttttgtggga agttaagcca aacttccaag atggtgttaa ggcttggttg     1320
gaaaacggtg tggtcacca cactgttgtt tctttgttct tgaccaccga tcaaatgatt     1380
acctacgcta agttggtcga cttggaatac gttgttatca agtaa                    1425
```

<210> SEQ ID NO 8
<211> LENGTH: 1701
<212> TYPE: DNA
<213> ORGANISM: Escherichia coli

<400> SEQUENCE: 8

```
atggctatcg ccattggttt ggatttcggt tccgattccg ttagagcttt ggctgttgat       60
tgtgctaccg gtgaagaaat tgctacctcc gttgaatggt atccaagatg gcaaaagggt      120
caattctgtg atgctccaaa caatcaattc agacaccacc aagagactca cattgaatcc      180
atggaagctg ctttgaaaac cgttttggct gaattgtccg ttgaacaaag agctgctgtt      240
gttggtattg tgttgattc caccggttcc accccagctc caattgatgc tgatggtaac      300
gttttggctt tgagaccaga attcgctgaa acccaaacg ctatgttcgt tttgtggaag      360
gatcacaccg ctgttgaaga agctgaagaa attaccagat tgtgtcacgc tccaggtaac      420
gttgattact ccagatatat tggtggtatc tactcctccg aatggttctg gctaaaatc      480 ttgcacgtta ccagacaaga ttccgctgtt gctcaatccg ctgcttcctg gattgaattg      540
tgtgattggg ttccagcttt tgttgtccggt actaccgac acaagatat tagaagaggt      600 agatgttccg ctggtcacaa gtccttgtgg cacgaatcct ggggtggttt gccaccagct      660
tcattcttcg atgaattgga cccaatttg aacagacact tgccatcccc attgttcacc      720
gatacctgga ccgctgatat tccagttggt actttgtgtc cagaatgggc tcaaagattg      780
```

```
ggtttgccag aatccgttgt tatttccggt ggtgctttcg attgtcacat gggtgctgtt      840
ggtgctggtg ctcaaccaaa cgctttggtt aaggttattg gtacttccac ctgtgacatt      900
ttgattgctg ataagcaatc cgttggtgaa agagctgtta agggtatttg tggtcaagtt      960
gatggttccg ttgttccagg ttttattggt ttggaagctg gtcaatccgc tttcggtgat     1020
atctacgctt ggtttggtag agttttgggt tggccattgg aacaattggc tgctcaacac     1080
ccagaattga aaactcaaat caacgcttcc caaaagcaat gttgccagc tttgaccgaa      1140 gcttgggcta agaacccatc cttggatcac ttgccagttg ttttggattg gttcaacggt     1200
agaagaaccc caaacgctaa tcaaagattg aagggtgtta tcaccgactt gaacttggct     1260
accgatgctc cattgttgtt cggtggtttg attgctgcta ctgctttcgg tgctagagct     1320
attatggaat gtttcaccga tcaaggtatc gctgtcaaca cgttatggc tttgggtggt      1380 attgccagaa agaatcaagt tatcatgcaa gcttgttgtg acgtcttgaa cagaccattg     1440
caaatcgttg cttccgatca atgttgtgct ttgggtgctg ctattttcgc tgctgttgct     1500
gctaaggttc acgctgacat tccatccgct caacaaaaga tggcttccgc tgttgaaaag     1560
accttgcaac atgttccga acaagctcaa agattcgaac aattgtatag aagataccaa      1620
caatgggcta tgtccgctga acaacactac ttgccaacct ccgctccagc tcaagctgct     1680
caagccgttg ctaccttgta a                                                1701
```

<210> SEQ ID NO 9
<211> LENGTH: 696
<212> TYPE: DNA
<213> ORGANISM: Escherichia coli

<400> SEQUENCE: 9

```
atgttggaag atttgaagag acaagtcttg gaagctaact ggctttgcc aaagcacaac        60 ttggttacct tgacctgggg taacgtttcc gctgttgata gagaaagagg tgttttcgtt       120
attaagccat ccggtgttga ttactccgtt atgaccgctg atgatatggt tgttgtttcc       180
attgaaaccg gtgaagttgt tgaaggtact aagaagccat cctccgatac cccaacccac      240
agattgttgt accaagcttt cccatccatt ggtggtatcg ttcacaccca ctccagacac      300
gctaccattt gggctcaagc tggtcaatcc attccagcta ccggtactac ccacgctgat     360
tacttctacg gtactattcc atgtaccaga agatgaccg atgctgaaat caacggtgaa      420
tacgaatggg aaaccggtaa cgttatcgtt gaaaccttcg aaaagcaagg tattgatgct     480
gctcaaatgc aggtgttttt ggttcactcc cacggtccat tcgcttgggg taagaacgct     540
gaagatgctc ttcacaacgc tatcgttttg gaagaagttg cttacatggg tatttttctgt   600 agacaattgg ctccacaatt gccagatatg caacaaaacct tgttggataa gcactacttg     660
agaaagcacg gtgctaaggc ttactacggt caataa                                696
```

<210> SEQ ID NO 10
<211> LENGTH: 22
<212> TYPE: DNA
<213> ORGANISM: Artificial Sequence
<220> FEATURE:
<223> OTHER INFORMATION: forward primer for pXYL2

<400> SEQUENCE: 10

```
aatggtcttg ggtcacgaat cc                                                22
```

<210> SEQ ID NO 11
<211> LENGTH: 23

```
<212> TYPE: DNA
<213> ORGANISM: Artificial Sequence
<220> FEATURE:
<223> OTHER INFORMATION: reverse primer for pXYL2

<400> SEQUENCE: 11
gctctgacca agtcgtaggc ttc                                                23
```